United States Patent [19]
Lin

[11] Patent Number: 5,252,834
[45] Date of Patent: Oct. 12, 1993

[54] PULSED AND GATED MULTI-MODE MICROSPECTROPHOTOMETRY DEVICE AND METHOD

[75] Inventor: Rui Lin, Corona, Calif.

[73] Assignee: Union Oil Company of California, Los Angeles, Calif.

[21] Appl. No.: 614,030

[22] Filed: Nov. 13, 1990

[51] Int. Cl.$^5$ .............................................. G01N 21/64
[52] U.S. Cl. ........................... 250/458.1; 250/459.1; 356/318
[58] Field of Search .................... 356/318, 317, 417; 250/458.1, 461.1, 461.2, 459.1

[56] References Cited

U.S. PATENT DOCUMENTS

| | | | |
|---|---|---|---|
| 4,058,732 | 11/1977 | Wieder | 250/461.1 |
| 4,198,567 | 4/1980 | Eneroth | 356/318 |
| 4,259,574 | 3/1981 | Carr et al. | 250/461.1 |
| 4,365,153 | 12/1982 | Seigel et al. | 250/461.1 |
| 4,645,342 | 2/1987 | Tanimoto et al. | 356/318 |
| 4,791,310 | 12/1988 | Honig et al. | 250/461.2 |

FOREIGN PATENT DOCUMENTS 8801379  2/1988  PCT Int'l Appl. ................. 356/318

OTHER PUBLICATIONS

Watson et al., "Simplification of Spectra by Electro-Optic Gating of the Radiant Emission from Laser-Produced Plasmas", J. Phys. E, 10 (12), 1977, pp. 1227-1228.

Moenke, "Über den Stand der Mikro-Emissions-Spektralanalyse mit Feskörperlasern", Messtechnik, Jan. 1968, pp. 13-18.

Rasberry, "Laser Probe Excitation in Spectrochemical Analysis. I: Characteristics of the Source", Appl. Opt. 6(1), Jan. 1967, pp. 81-86.

Primary Examiner—Carolyn E. Fields
Attorney, Agent, or Firm—Gregory F. Wirzbicki; William O. Jacobson

[57] ABSTRACT

A short pulse of laser excitation and a synchronized gating time control of a fluorescence spectrograph detector are combined with a microscope, precise focusing and delivery optics, multi-mode illumination means, cooling, and temperature controls to form a new microspectrophotometry system. The gating control can block detection of any unwanted excitation radiation, such as nearly instantaneous (within $10^{-12}$ seconds) emissions after the sample is pulse excited and delayed emissions (after $10^{-7}$ seconds) after the sample is pulse excited. The gating also allows delayed emissions to be separately isolated. The microscopic focusing, pulse excitation and time segregation of detected emissions achieves a new level of precision in the detected structural spectra and property measurements not generally achievable for composite samples by prior art methods and devices.

24 Claims, 9 Drawing Sheets

PULSED AND GATED MULTI-MODE MICROSPECTROPHOTOMETRY DEVICE AND METHOD

FIELD OF THE INVENTION

This invention relates to spectral radiation analysis of emissions from irradiated samples. More specifically, the invention relates to microscopic devices and methods for the combined optical and spectral emission analysis of geological, biological and other organic polymeric samples composed of different types of microscopic particles or interest, such as kerogen contained in petroleum source rocks.

BACKGROUND OF THE INVENTION

Many geological, biological and other solid materials are heterogeneous composite structures formed from interrelated, but microscopically and chemically discrete particles or cells. The commercial use of these materials can require information related to the chemical and physical properties of the material's individual microscopic particles. However, conventional laboratory analysis of a sample of these composite materials, such as a wellbore core sample is performed on a bulk basis. Analysis of these samples is commonly accomplished by a variety of methods, including fluorescent spectroscopy, fluorometry and fluorescent microscopy.

Fluorescent techniques use an energy source, such as incident continuous wave ultraviolet (UV) irradiation, to excite a sample to cause fluorescent emissions from the sample. Fluorescence is the emission of radiant energy (such as light) as the excited electrons of an atom or molecule within the sample return to a lower or ground state after being promoted to a higher energy state by absorption of the exciting energy. Fluorescent radiations are normally distinct from light absorption, transmission and reflection with respect to time (from absorption of incident irradiation), direction, intensity and wavelength.

Molecules contained in the materials can possess ground state and many excited electron states. Electron transitions between the many electron states cause fluorescent emissions to be at several different intensities, wavelengths, and times after absorption, the emissions forming a spectral structure. The fluorescent spectral structure can be quite complex for materials having heterogeneous chemical structures.

Conventional fluorescence spectroscopy and photometry are commonly used to detect the composition and concentration of organic compounds in diluted solutions. The emission spectra of these compounds, which normally possess de-localized electrons, can display vibrational bands as a result of transitions between the different electron states. However, for a majority of solid composite samples, these techniques may not yield molecularly resolved spectral or intensity information.

If a fluorescent analysis of a composite sample having many constituents is desired, the analysis method and device becomes much more complex. Conventional fluorescence analysis devices typically use continuous wave mercury emission as illumination and excitation source. These are primarily designed for homogeneous samples (typically dissolved in a diluted solution) and are not normally used for composite solid samples without process and/or apparatus changes. These devices bulk illuminate (i.e., energize many particles within the entire sample) and measure bulk fluorescence (i.e., the intensity and spectral emissions of the entire sample), producing potentially overlapping spectral structures from a composite sample.

One composite sample analysis technique involves splitting the sample. A small sample portion is prepared and isolated for optical analysis (microscopic examination) and the other portion of the sample is then used for a separate bulk chemical analysis. This two step process tends to be slow, complex, and unreliable.

Another composite sample analysis technique is fluorescence microscopy. In one embodiment of the fluorescence microscopy method, bulk illumination of several particles of the sample is accomplished, typically by a high pressure mercury arc lamp. The integration of a microscope, a scanning monochromator, and a photomultiplier detector, forms a microscopic detector which can be directed to a relatively small area of interest. With the use of a measuring diaphragm, the focused detection of an illuminated microscopic particle within the sample allows microspectrophotometry to be performed on the fluorescent emissions. Quantitative measurement of the detected fluorescence intensity and spectral distribution provides information regarding one or more fluorescing particles.

However, because several particles of the sample are illuminated, emissions from unwanted particles or portions of the system cannot always be totally excluded. Other sample portions can produce significant fluorescence within the sample which may be emitted towards the focused detector. It may not be possible to accurately segregate the contribution(s) of each type of particle from the mixed detection information generated by this method. The detector focus area of interest may also not be able to be reduced to isolate a single particle's emissions.

Secondly, as a consequence of the broad excitation and absorption bands, continuous-wave excitation, and long exposure time (generally in the order of several milliseconds to several seconds), the fluorescence spectrum obtained by conventional fluorescence microscopy may not be completely resolved, and the spectrum typically provides little chemical information regarding the microscopic particles of interest.

As an alternative to this fluorescence microspectrophotometry method, a continuous wave laser beam can be used as a source of irradiation energy. This is illustrated in U. S. Pat. Nos. 4,616,133. The laser irradiation process essentially irradiates an area of interest within a sample with ultraviolet (UV) radiation from a helium-cadmium or nitrogen laser, separates the resulting emission spectrum into wavelength segments, and measures the intensities within each wavelength segment.

The laser selectively excites certain constituents or particles in the sample. The monochromaticity of the laser also tends to limit the excitation states of specific molecules whose absorption bands coincides with the laser emission. A Xenon lamp coupled with a scanning monochromator provides a tunable continuous wave source which can also be used to selectively excite constituents or selectively achieve certain excitation states. Measured emissions (intensity in a given direction within a wavelength segment) are compared to one or more reference emissions to identify properties of particles in the area of interest.

Prior work indicates that the fluorescent emissions are not always constant, but may change over extended exposure time. Although most fluorescence is relatively rapid, delayed fluorescence or phosphorescence is also common. Exciting irradiation can thus produce overlapping rapid and delayed emissions over time. In addition, other changes in emission intensity and wavelength appear to be caused by absorption of laser energy which is not emitted as fluorescence. Temperature increases, oxidation or other reactions are some of the results of the absorption of laser energy. These time dependent factors can cause significant changes to the spectral structure over time, such that unique spectral time changes can also be used for identification purposes.

Even with microspectrophotometry and the use of a continuous wave laser, the composite samples create spectral analysis problems. First, the use of a continuous wave laser cannot separate fluorescence from slower emissions. The temporal behavior of fluorescence cannot be precisely examined, especially in the first hundred nanoseconds. Second, the continuous excitation causes photochemical reactions of the composite samples which may give rise to chemical information unrelated to the original chemistries. Third, a continuous-wave UV laser produces fluorescence emission with little chemical information, since the fluorescence spectra are almost as broad and unstructured as induced by mercury excitation.

SUMMARY OF THE INVENTION

A fluorescent microspectrophotometry apparatus and method for obtaining a much more distinct spectral structure from particles within a composite sample is presented. The apparatus and method also now allows time isolation of a microscopic particle's fluorescent emissions as well as intensity and wavelength information. This is accomplished by providing a short burst of pulsed and tunable laser excitation and a synchronized gating control of a fluorescence microspectrograph detector. The pulsed laser, and synchronized and gated control components are combined with a microscope, precise laser microbeam and emission focusing and delivery optics, multi-mode illumination means, cooling, and temperature controls to complete the system. The synchronized gating blocks detection of unwanted emissions. The gating also allows delayed emissions, such as delayed fluorescence and phosphorescence, to be isolated and measured. The short pulse of excitation energy also minimizes unwanted temperature and spectral changes over time.

The synchronization of single pulse excitation with the gatable microspectrograph/detector and time isolation of spectral emissions allows the detector system to block detection of, for example, delayed emissions, and to detect the desired emissions within certain time segments after the sample is excited. The gated system opens to detect only the normally rapid fluorescent emissions, i.e., emissions that most frequently take place after $10^{-12}$ seconds and before $10^{-7}$ seconds (100 nanoseconds) as measured from (i.e., synchronized with) the leading edge of the excitation pulse. The gated system can also separately detect delayed fluorescence or phosphorescence, most of which occurs after $10^{-7}$ seconds from pulsed excitation.

The microscopic beam focusing, laser pulse delivery and excitation, and time synchronization and segregation of detected emissions achieves a new level of spectral and properties determination precision for microscopic particles in composite samples. Although time and area ranges are theoretically unlimited, the preferred system can irradiate a microscopic particle/area of interest as small as $2 \times 10^{-7}$ cm$^2$ with a pulse as short as 15 nanoseconds, detect emissions from the particle in a gated time window as little as 100 nanoseconds long beginning anywhere up to 10 milliseconds after the initiation of the excitation pulse and can detect emissions from an irradiated area as small as $2 \times 10^{-7}$ cm$^2$. The improved apparatus and method should also minimize the cost and time required for sample preparation and analysis, sample positioning, separate focusing, and minimize analysis errors by being tolerant of off-design conditions.

The time isolation capabilities coupled with a pulsed laser and a continuous-wave source can be used to study the photochemistry of composite materials comprised of microscopically and chemically discrete particles. The system can permit time-resolved photochemical alteration with time of fluorescence with one nanosecond resolution.

The tunability of the laser also allows selection of different wavelengths. Since different molecular structures possess different absorption spectra, this tunability further permits excitation of selective molecular species. Moreover, the short but intense laser excitation and microbeam delivery and focusing optics allow fluorescence analyses of some microscopic particles which cannot be induced by conventional means to produce sufficient fluorescence for detection. One example of this is sample containing gas-prone and non-productive kerogens.

The apparatus can also be used to create new spectral data opportunities, such as multi-pulsing and separate gated times for fluorescent emissions in different directions, such as polarized fluorescence. At the same time, the system retains the more conventional illuminations, non-pulsed laser excitation, and non-gated detector analysis capabilities. The combination of synchronized pulsed micro-illumination/micro-detection and more conventional illumination/detection provides a powerfully improved microspectrophotometry tool, especially useful for complex constituents of particles within composite samples.

BRIEF DESCRIPTION OF THE DRAWINGS

In these Figures, it is to be understood that like reference numerals refer to like elements or features.

DETAILED DESCRIPTION OF THE INVENTION

Figure 1:
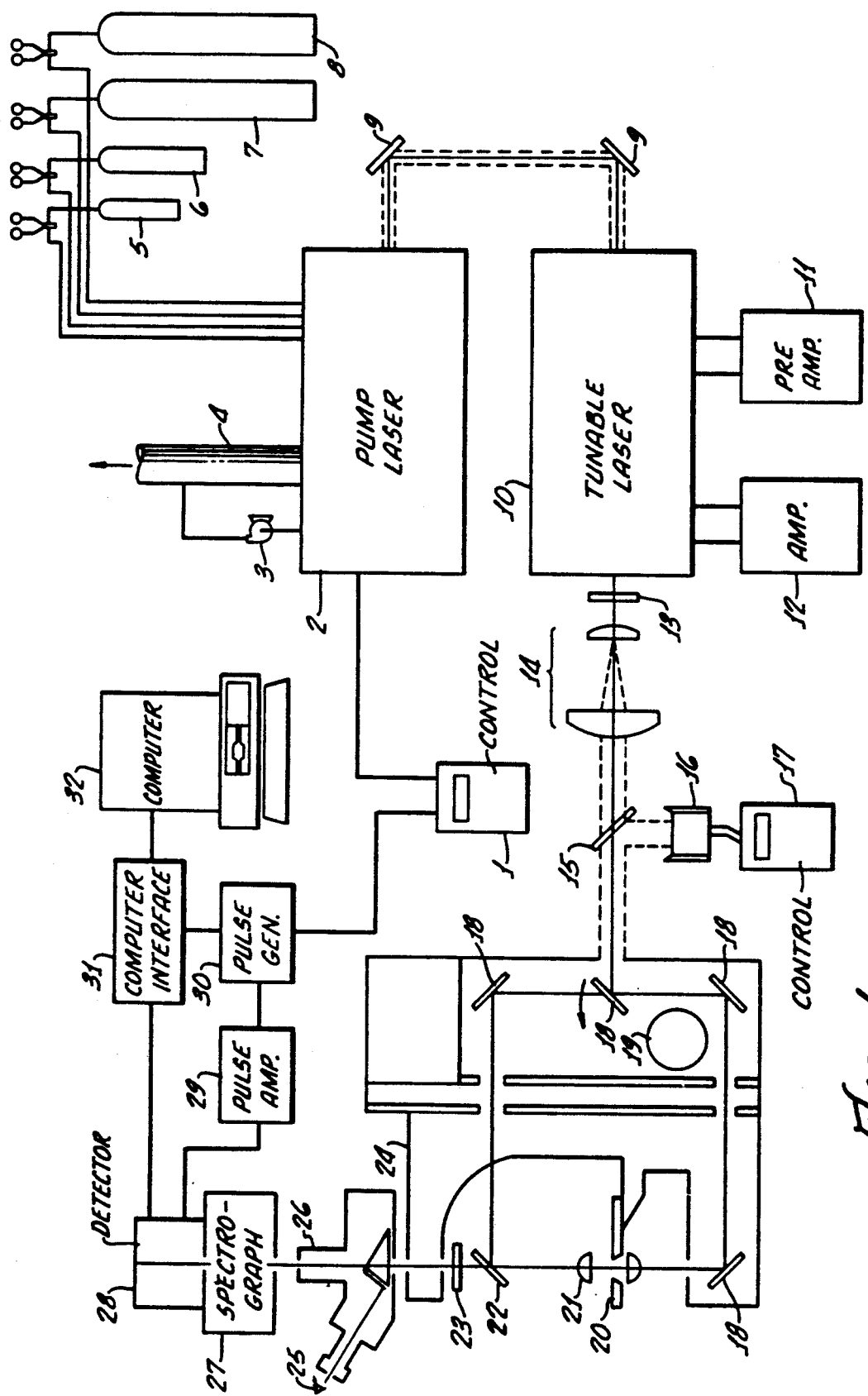
FIG. 1 shows a schematic of the improved microspectrophotometry system.

FIG. 1 shows a schematic of a new microspectrophotometry system. The system uses a pulsed beam output of an excimer (or exciplex) laser 2 controlled by controller 1. The excimer laser 2 generates a short burst of irradiation or a short laser pulse to pump or excite a tunable dye laser 10. An excimer laser obtains its name from a process where lasing occurs from an excited state diatomic complex, such as XeCl complex. The complex is generally formed by a chemical reaction between rare gas (Xe+) and halide (Cl−) ions produced by a rapid electrical discharge in a buffer and inert gas carrier. Since the XeCl complex has a very short lifetime, it decays rapidly and produces lasing photon emissions.

Although lasers of other wavelengths are available, typically below 400 nm, the preferred XeCl excimer laser 2 produces a pulsed coherent emission at about 308 nm wavelength. The single excimer pulse duration is approximately 17 nanoseconds. Although infinitely shorter and longer pulse durations are theoretically possible, a pulse duration of less than 20 nanoseconds is preferred, most preferably less than one nanosecond. A train of excimer pulses is also preferred for some sample compositions. Although higher and lower repetition rates and energies can also be used, the preferred adjustable repetition pulse rate ranging from 1 to 100 Hz. A train of pulses each having relatively constant energies is preferred, but a range of pulse energies within a train is also possible. The preferred single excimer pulse energy nominally 200 mj or more. As a safety measure, the controller 1 is interlocked with a personnel access means, such as a door, shutting off the excimer laser when the door is opened.

The preferred excimer laser requires a supply of rare, inert, buffer and halogen containing gases. An exhaust conduit 4 is used to pump air (and other gases) from the laser head which may contain leaked gases used inside the laser reservoir. A vacuum pump 3 and the exhaust conduit 4 are also used to purge reservoir in the excimer laser 2 after the mixture has been used. The preferred halogen containing gas (5% HCl, 1% H and 94% He) is a corrosive mixture supplied by a halogen gas source 5 comprising a cylinder and regulator. Corrosion resistant materials, such as stainless steels, are used for halogen gas carrying tubing, cylinder, and regulator construction. The rare gas source (cylinder and regulator) 6 supplies laser grade Xe (99.99% purity). The buffer gas (Ne) source 7 (cylinder and regulator) and inert gas (He) source 8 cylinder and regulator supply Ne and He gases, respectively, at 99.999% purity.

The output pulses from the excimer laser are deflected by two high UV mirrors 26 mounted at 45 degree angles to direct the excimer pulsed pump energy to dye laser 10. The dye within dye laser 10 is a molecular dye, such as polyphenyl 1, dissolved in a solvent such as ethyl glycol and methanol. The solvent serves as a diluting and cooling medium, reducing thermal decay and quenching effects of the dye molecules.

After the dye molecules absorb the pump excitation energy from the excimer laser beam, they are raised to the excited states. The excited molecules can then release the absorbed energy in several different processes. Radiationless energy release or transition dissipates some of the absorbed energy into thermal vibration, but the energy release portion of primary interest is released as stimulated emissions. There are two forms of emissions, non-coherent spontaneous emission and coherent emission. Non-coherent emission is random in direction and phase, and is generally lost from the system. The stimulated or coherent emission emits photons with the same phase and direction, amplifying the light signals coherently. As the coherent light beam passes through the dye mixture, it stimulates emission of more photons of the same energy, phase and direction.

As the excimer pump beam enters into the dye laser 10, it is split toward a pre-amplifier cuvette and toward an amplifier cuvette (not shown for clarity) within the dye laser 10. The pre-amplifier dye circulator 11 and amplifier dye circulator 12 pump dye solutions through respective dye flow cuvettes in the dye laser 10. The output dye laser beam is collimated and shaped into a round beam 2-3 mm in diameter.

At least a few hundred laser dyes are currently commercially available. Table 1 lists tuning ranges and solvents for some Lambdachrome ® dyes, supplied by Lambda Physik GmbH, D-3400, West Germany.

TABLE 1

| LAMBDACHROME TUNING RANGES AND SOLVENT | | |
|---|---|---|
| Dye Number and Title | Tuning Range (nm) | Solvent |
| LC 3300 BM-Terphenyl | 312-343 | CH |
| LC 3400 p-Terphenyl | 332-350 | DI |
| LC 3590 DMQ | 346-377 | DI |
| LC 3600 QUI | 368-402 | DI |
| LC 3860 BiBuQ | 367-405 | DI |
| LC 4000 PBBQ | 386-420 | DI |
| LC 4090 DPS | 399-415 | DI |
| LC 4100 Stilbene | 405-428 | EG |
| LC 4200 Stilbene 3 | 412-442 | ME |
| LC 4400 Courmarin 120 | 423-462 | ME |
| LC 4500 Courmarin 2 | 432-475 | ME |
| LC 4700 Courmarin 47 | 440-484 | ME |
| LC 4800 Courmarin 102 | 460-510 | ME |
| LC 5000 Courmarin 307 | 479-553 | ME |
| LC 5210 Courmarin 334 | 506-537 | ME |
| LC 5400 Courmarin 153 | 522-600 | ME |
| LC 5900 Rhodamine 6G | 569-608 | ME |
| LC 6100 Rhodamine B | 588-644 | ME |
| LC 6200 Sulforhodamine B | 594-642 | ME |
| LC 6400 Rhodamine 101 | 614-672 | ME |
| LC 6500 DCM | 632-690 | DMSO |
| LC 7000 Rhodamine 700 | 701-768 | ME |
| LC 7100 Pyridine 1 | 670-760 | DSMO |
| LC 7270 Oxazine 750 | 735-796 | DSMO |
| LC 7300 Pyridine 2 | 695-790 | DSMO |
| LC 8000 Rhodamine 800 | 776-823 | DSMO |
| LC 8400 Styryl 9 | 810-875 | DSMO |
| LC 8500 HITC | 837-905 | DSMO |
| LC 8800 IR 144 + IR 125 | 842-965 | DSMO |
| LC 9210 IR 125 | 890-960 | DSMO |
| LC 9300 IR 140 | 882-985 | DSMO |

Lasing in the dye laser 10 is accomplished by using an optical cavity or resonator which defines a self-repeating or amplified optical path through the active medium (i.e., the dye solution) between a mirror and grating (not shown for clarity). A standing wave of essentially one wavelength can be generated when the optical cavity distance between the grating and mirror is an integer multiple of ¼ the standing wavelength. Tuning of the dye laser 10 is accomplished by moving (e.g., turning) the grating which changes the grating to mirror cavity dimensions and therefore the wavelength of amplified emissions.

The dye used in dye laser 10 may be one of a series depending upon the particle types, sample, sample preparation, and spectral structures desired. Although the maximum number of dyes that can be used is essentially unlimited, usually no more than 3 dyes are needed to precisely define properties of a geological sample.

The dye laser output pulse is passed through an optical attenuator 13 which adjusts the level of excitation energy suitable for microscopic excitation and optics. The attenuated dye laser beam pulse then travels through a beam expander and collimating optics 14. The expansion and collimating of the dye laser beam makes it easier to manipulate and later concentrate the beam to form a microbeam spot on the sample surface portion which is of interest, e.g., the particle of interest.

An optical attenuator 13 is preferred in order to adjust the laser pulse energy so that the microscope and laser beam delivery optics are not destroyed by the short, but very intense laser energy. Normally, a circular linear-wege neutral density filter or a polarizer can be used, for example, the Melles Griot 03FDC 001/E.

The beam expander portion of optics 14 is desired because the laser beam can be expanded for uniform illumination when it is recondensed by the microscope objective lenses. Secondly, the expanded beam is easier to manipulate within the microscope. Both mounted and unmounted beam expanders can be used. An expansion ratio of at least $2\times$ is preferred, typically $10\times$, although other ratios may be used. The beam expander and collimating optics 14 can consist to two plano-convex lenses such as the Melles Griot 01 LQF023 and 01LQF244 synthetic fused silica lenses.

The collimated dye laser beam then passes through a beam splitter 15 where a small portion (<10%) of the beam energy is extracted towards an energy probe 16 and joulemeter 17 for measuring the energy of the irradiating beam. The energy probe 16 and joule-meter 17 allow the system user to monitored the system while the main portion of the pulsed beam is directed to the microscope body 24 and associated internal reflection mirrors 18.

Since the fluorescence intensity and possibly spectral structure can be dependent upon the energy levels of the impinging laser pulses, a single pulse or pulse-to-pulse energy level monitoring is desirable. For example, in determining petroleum source rocks or coal ranks, the intensity emitted from kerogens and macerals can be used to evaluate the maturity of the rocks or coals. Secondly, time-resolved fluorescence yield and spectral distributions may also need to be corrected for the energy level differences of the impinging laser pulses. Although other means for measuring pulse energy are possible, the preferred embodiment uses the beam splitter 15 to extract a small portion of the laser pulse and reflect the extracted portion into a coupled energy probe 16. An example of a beam splitter and energy probe is a Molectron JS50Q beam splitter coupled with a J50 energy probe and JD500 Joulemeter.

After extracting and measuring the collimated beam's energy, the dye laser beam is directed to a microscope body 24. In the preferred embodiment a modified Leitz MPV 3 microscope is used, allowing a variety of illuminations and excitation options. Several lamp housings (one shown for clarity) 19 allow white light, UV and blue light illumination and excitation of a sample located on the microscope stage 20, for example using a high pressure mercury arc lamp with a HBO 100 lamp housing and a tungsten lamp for both UV and white light illumination. For pulsed excitation, the major portion of the laser beam from the splitter 15 enters the body 24 from a back port coaxial to the microscope optical axis (shown as a line between an eyepiece 25 and a pair of objective lenses 21). Rotation (as shown by arrow) of the first internal mirror 18 proximate to the beam splitter 15 allows choosing between a transmitted beam mode (where the position of the first internal mirror 18 is as shown, reflecting irradiating beam initially downward) and a reflected beam mode (as shown by alternative path of the irradiating beam initially directed upward from first internal mirror 18).

When the system is in a reflected beam mode, the upwardly reflected beam is reflected again by another one of the internal mirrors 18 towards a dichroic mirror 22. The dichroic mirror 22 is efficient in reflecting certain radiation frequencies such as UV light (i.e., reflecting the excitation laser beam) while transmissive to other radiation frequencies such as visible light (from the sample). The dichroic mirror 22 therefore reflects the pulsed UV laser beam through the upper objective lens 21 to the area of interest (e.g., a particle) on the surface of a sample supported by the microscope stage 20.

When the transmitted mode is desired, the first of the internal mirrors 18 system reflects the incoming pulsed beam downward. Other of the internal mirrors 18 then reflect the UV irradiating beam towards the sample on the microscope stage 20 from below. Fluorescent emissions from the sample which are directed towards the phototube 26 pass through the objective lens 21, dichroic mirror 22, and barrier filter 23. The dichroic mirror 22 may also be removed from the optical axis of the microscope body 24 in this mode.

The dye laser beam optics (expander, collimator, attenuator, and focus devices) allow an area within the boundaries of a microscopic particle to be irradiated. The surface area irradiated is typically less than a square millimeter, and as small as $2\times10^{-7}$ cm$^2$. Even smaller areas are also theoretically possible.

Fluorescent emissions from the sample which emanate in the direction of the eyepiece 25 are transmitted through the upper objective lens 21, the dichroic mirror 22, and a barrier filter 23 to a phototube 26. The barrier filter 23 is a long pass filter, allowing only the desired fluorescence emission frequencies to pass through and blocking any reflected excitation from reaching the detector or eyes at eyepiece 25.

Filters are conventionally desirable to isolate and reflect excitation bands, and to block excitation light from reaching the detector 28. For conventional mercury excitation, at least three filters are desirable, an excitation filter, a dichroic mirror 22 and a barrier filter 23. Although other combinations may be used, examples of conventional filter combinations for visual examination and identification of microscopic particles include a Leitz Ploemopak Filter Block H2 combination (consisting of a band pass filter BP 390–490 nm, a dichroic mirror RKP 510 nm, and a barrier filter LP 515nm), and an H3 combination (consisting of a band pass filter BP 420–490 nm, a dichroic mirror RKP 510 nm, and a barrier filter LP 515 nm). For mercury-induced spectral fluorescence analysis, Filter Block A (consisting of a band pass filter BP 340–380 nm, a dichroic mirror 400 nm and a barrier filter LP 430 nm) is used.

For a pulsed laser excitation, the lasing emission is already monochromatic and also may by blocked out by the gated detector, therefore no excitation or other filters are necessary. Only a dichroic mirror to efficiently reflect the laser beam (in the reflected mode) and a barrier filter to block reflected laser excitation are typically used.

The filtered emissions then pass through the phototube 26 to the entrance slit of the spectrograph 27. At the exit of the preferred phototube is a small condensing lens (not shown). The emitted fluorescence microbeam is focused by the condensing lens into the entrance slit of the spectrograph 27, enabling efficient and rapid detection of fluorescence.

The emissions entering the entrance slit of spectrograph 27 are isolated according to wavelength by a grating (not shown) after reflection and collimating inside the spectrograph 27. After emissions within the isolated range of wavelengths emerges from the exit slit of the spectrograph 27, they enter and are detected by an intensified photodiode array in detector 28. The preferred photodiode array detector is an EG&G PARC 1455B-700-HQ intensified and blue enhanced. This array detector has 1024 elements, 700 of which are active. The detector has a gatable, proximity focussed microchannel plate (MCP) image intensifier. The intensifier generates more than one analog-to-digital conversion (ADC) count for each detected photon.

The synchronization of the firing of the excimer laser 2, excitation pulse from dye laser 10, and gating of the spectrograph detector 28 is accomplished by the electronic controller 1, a pulse generator 30 for generating a control pulse, a pulse amplifier 29 for amplifying the control pulse, a detector interface 31, and a computer 32. The synchronized sequence is programmed so that the exciting dye laser pulse is synchronized with the gating window of the detector 28.

Figure 2:
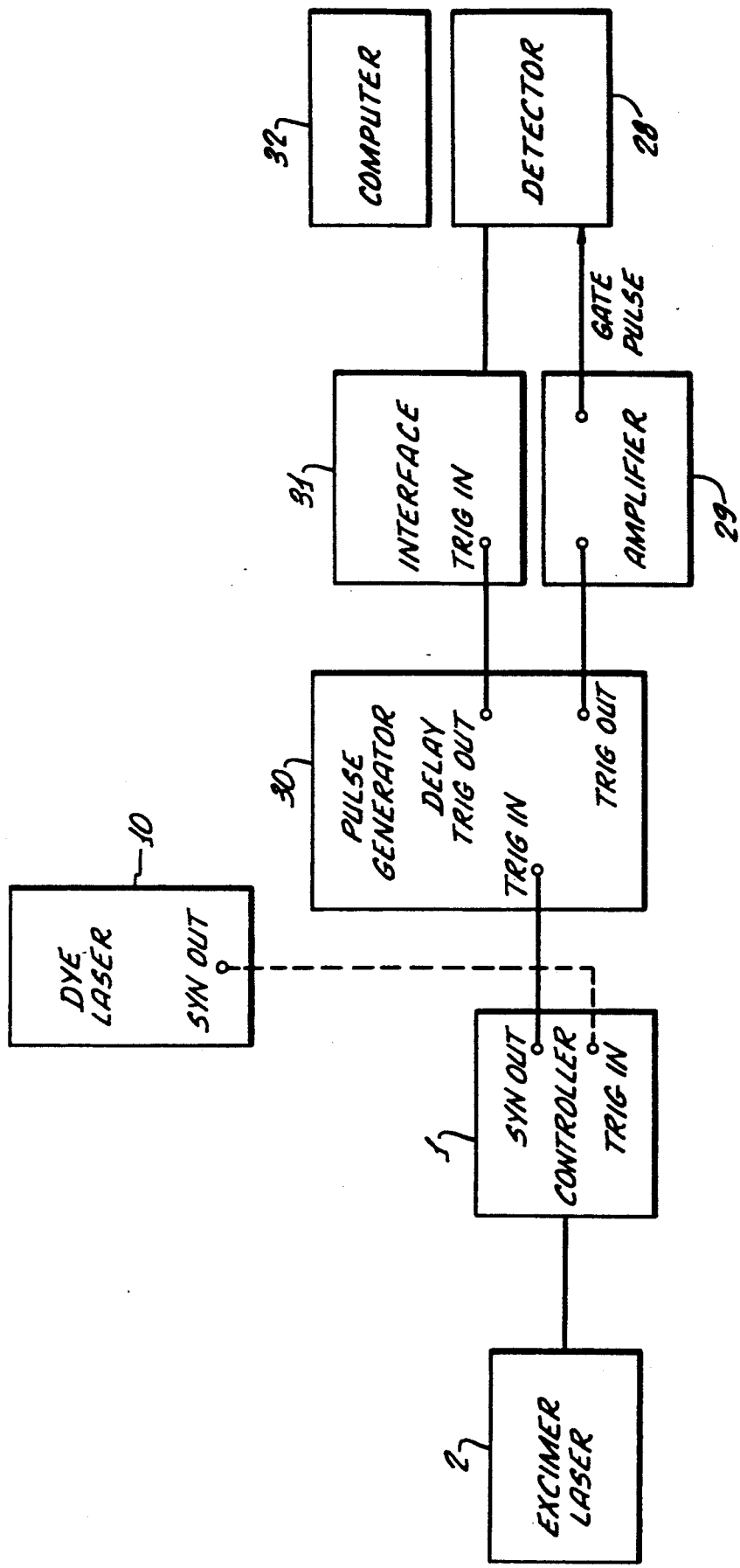
FIG. 2 shows a control schematic of the improved microspectrophotometry system.

The logic flow for control of synchronization and detector gating is shown schematically in FIG. 2. Synchronization and gating is accomplished by control or triggering Transistor-Transistor-Logic (TTL) pulses. When the controller 1 is activated to initiate a dye excitation pulse from excimer laser 2, it also generates (as shown from SYN OUT) a control or logic 1 TTL pulse to trigger the pulse generator 30 (as shown at TRIG IN). Upon receiving the leading edge of the logic 1 TTL pulse, the pulse generator 30 begins a delay period initiated through the detector interface 31 and computer 32.

The delay period is computer program controlled. It was experimentally determined that the preferred dye laser pulse begins approximately 570 nanoseconds after the leading edge of the TTL logic 1 pulse. This information is entered in the computer program. The delayed control pulse triggering of the pulse amplifier 29 and diode array within the detector 28 allows detector 28 to be synchronized with the exciting pulse from the dye laser 10. Thus, a delay of 570 nanoseconds was programmed so that only fluorescence emissions induced by the dye laser 10 were detected by the gate controlled detector 28.

The control pulse from the pulse generator 30 (a Delay Trig Out terminal) is also sent to the detector interface 31 to prepare for active scanning and reading of the signals. This is accomplished by having a read and reset command in the data acquisition program before a scan is executed, as shown in this case as Trig In. Upon receiving this pulse, the charged diode arrays in detector 28 are read and reset. The analog to digital converted data are then sent to the computer 32 for processing.

An additional delay can also be programmed. If only delayed fluorescence and phosphorescence is desired to be detected, a program delay of approximately 670 nanoseconds is programmed since a majority of fast fluorescence occurs within 100 nanoseconds of the excitation irradiation. If only fluorescence detection after termination of most of the excitation irradiation is desired, a program delay of approximately 585 nanoseconds is programmed since the dye laser pulse lasts approximately 15 nanoseconds. Although time delay (or advance) adjustment is theoretically unlimited, the preferred programmed delay is adjustable from about 500 nanoseconds to 3 milliseconds.

The controls also set the time window or gate width, i.e., the length of time the detector 28 is detecting. For example, a gate width of 100 nanoseconds (after an approximately 570 nanosecond delay) would detect a majority of the fast fluorescence from the irradiated sample. Although the control pulse width is theoretically unlimited, the preferred programmed pulse width was adjustable from approximately 100 nanoseconds to 10 ms.

Several units in the system typically need to be cooled and temperature controlled while in operation, specifically the excimer laser 2, the pre-amplifier and amplifier dye circulators of the dye laser 10, and the photodiode array detector 28. Although the preferred embodiment temperature controls are described, many conventional alternative temperature controls may also be used. Preferably, cooling is accomplished by circulating chilled water (not shown) at about 13° C. to these units. The excimer laser 2 was typically temperature controlled by a chilled water flow rate of between 4 and 5 liters/minute, the dye circulators 11 and 12 by a flow rate of between 1 and 2 liters/minute, and the diode array detector 28 by a flow rate of approximately 1 liter/minute. It is especially advantageous to cool and control the diode array detector head of detector 28. The detector head was typically controlled to −25° C. by use of a thermoelectric cooler discharging heat into the 13° C. circulating chilled water. It may also be advantageous to cool the sample on stage 20 to cryogenic temperature.

The invention satisfies the need to obtain a more precise spectral structure of fluorescent emissions and to provide new composite sample analysis capabilities. It achieves these precision and added capabilities primarily by: 1) micro-focusing of short laser pulses of excitation irradiation tunable to different wavelengths within narrow bands of frequencies; 2) a gated and micro-detecting fluorescent emission detector; and 3) a means for synchronizing the gating and excitation pulses. The resulting emission spectral structure avoids intensity and wavelength errors caused by extraneous emissions and can now be segregated as to time. The invention minimizes spectral overlapping due to illumination and excitation of multiple components. The invention permits fast fluorescence analysis of a microscopic particle with very short exposure times, e.g., 100 nanoseconds. The invention allows separate measurement of delayed fluorescence and phosphorescence, fluorescent emissions in different directions and modes, and coordination of conventional optical and fluorescent analysis. Further advantages of the invention include: safety (e.g., interlocked excitation), reliability (e.g., avoids unwanted emission errors); and reduced cost (integrated one step analysis).

Although the preferred electronic controls are described, other configurations of control pulses, gating, reset, read, and delay controls may also be used. Still other alternative embodiments are also possible, including: alternative sources of UV sources instead of the excimer laser, such as flashlamps, frequency-doubled Nd:YAG and ion lasers; a plurality of detectors for different emission directions or wavelength; extending the computer controls to excitation beam focusing or scanning and sample cooling; combining more components within a single housing; and separating the excitation beam to excite different samples or portions of a sample.

The invention is further described by the following examples which are illustrative of specific results when using the invention and are not intended as limiting the scope of the invention as defined by the appended claims.

EXAMPLE 1

Example 1 is derived from testing samples formed by molding particles composed of one of several polycyclic aromatic hydrocarbon (PAH) compounds in an epoxy resin binder. A surface of the sample was polished for microscopic and fluorescence analysis. A solid PAH sample composed of particles having varying dimensions from approximately several square microns to over one hundred square microns was placed on a microscope stage in a system similar to that illustrated in FIG. 1. All measurements of solid particles were performed within the boundaries of a microscopic particle of interest so that fluorescent contributions from the epoxy resin binder were virtually eliminated.

The particle of interest was irradiated with a series of excitation pulses from the excimer laser and dye laser combination similar to as previously discussed. The detector was gated to detect fast fluorescent emissions (a delay of approximately 570 nanoseconds and a gate width of approximately 100 nanoseconds). The spectral results were compared to samples of liquid PAH compounds in a dilute solution contained within a quartz cuvette when irradiated by more conventional continuous wave mercury lamps.

Figure 3A:
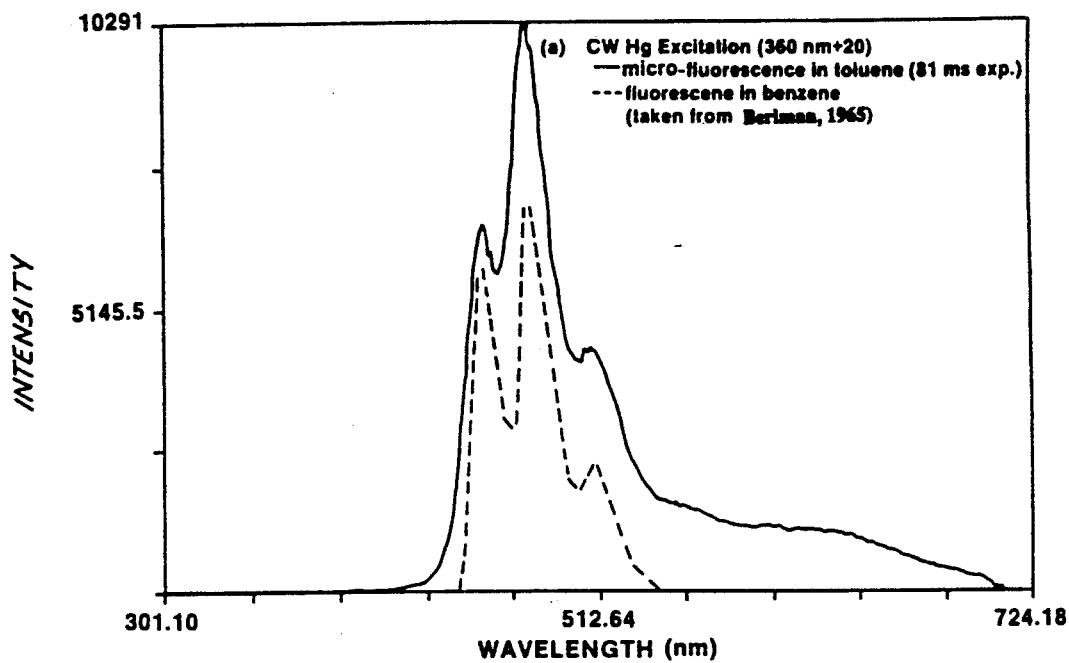
FIGS. 3a, 3b, 4a, 4b, 5a, and 5b show graphical results of using the microspectrophotometry system on polcyclic aromatic hydrocarbons (PAH) materials.
Figure 3B:
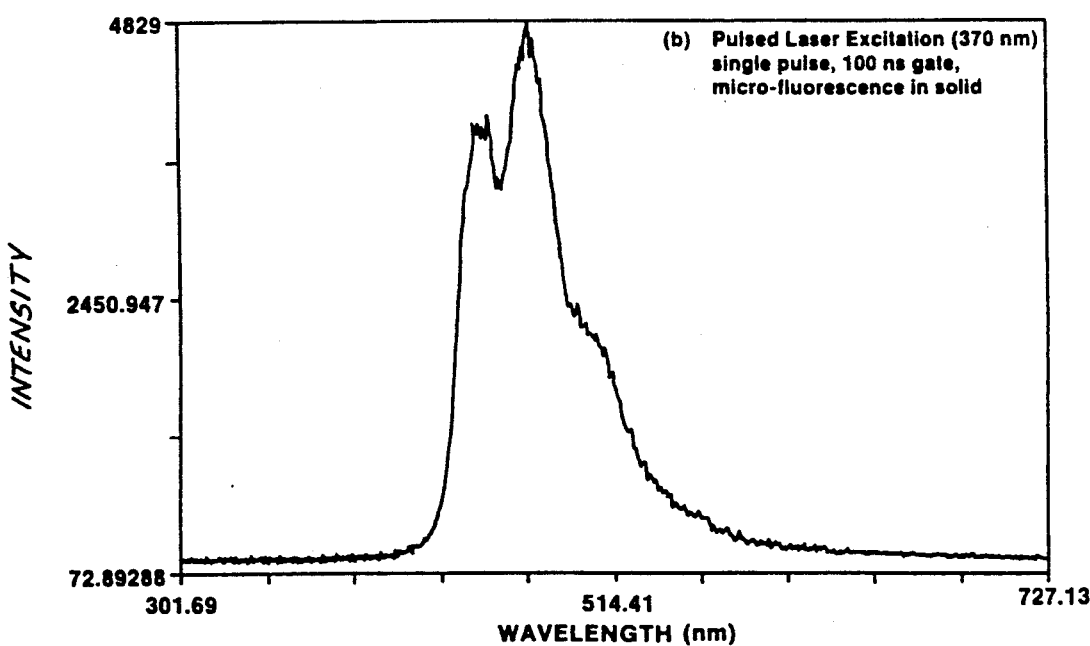

A sample of the spectral results is shown in FIG. 3. The top (a) portion of FIG. 3 shows the spectral results (as solid line) when analyzing a liquid perylene (a PAH) sample dissolved in toluene. This is compared to similar published data from perylene dissolved in benzene. Comparison to published data shows that the three vibronic bands of the published data (Berlman, 1965) were consistently detected by the system and confirmed general system operation.

The lower (b) portion of FIG. 3 shows one of the solid sample results from a single excitation pulse. The three vibronic bands are again detectable and small peaks on top of the three broad bands are now also resolved and detectable. The magnitude of these peaks appears to also be three to four times stronger than random background noise. This result can be compared to spectral results produced by a tunable dye laser having greatly reduced bandwidths when a PAH compound was vapor deposited in an alkane matrix (Maple et al., 1980).

A minor difference can be noted that the 0-2 transition vibronic band is less distinct for the solid than the liquid solution data. Although the cause of this difference is not certain, the less distinct transition results may be due to the solid form and gated detector, i.e., the invention results may be a more accurate spectral structure of the sample.

Figure 4A:
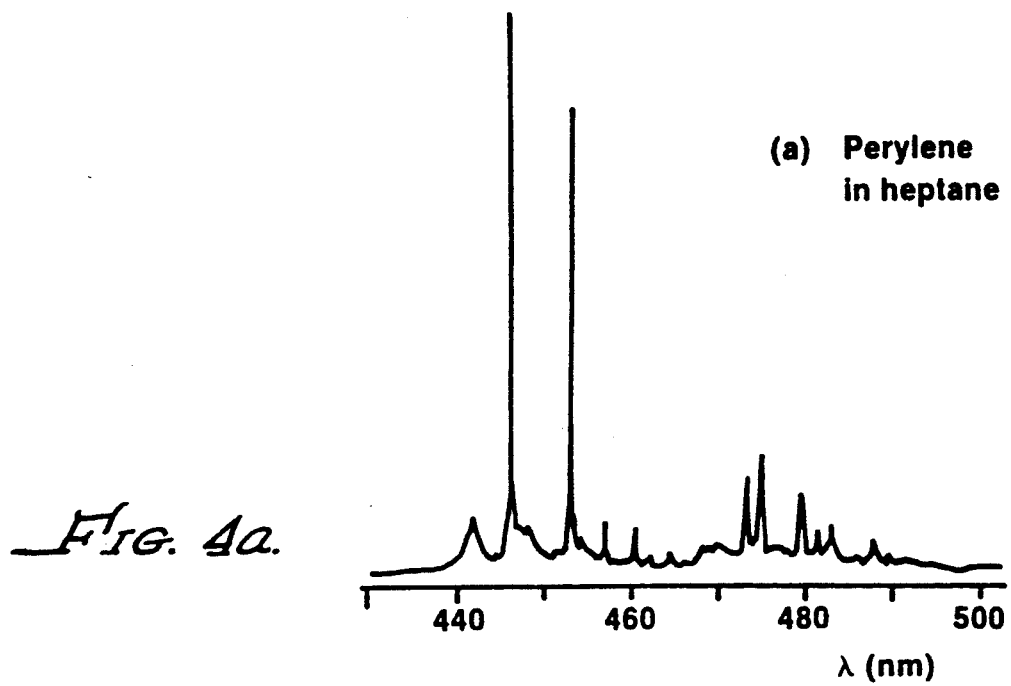
Figure 4B:
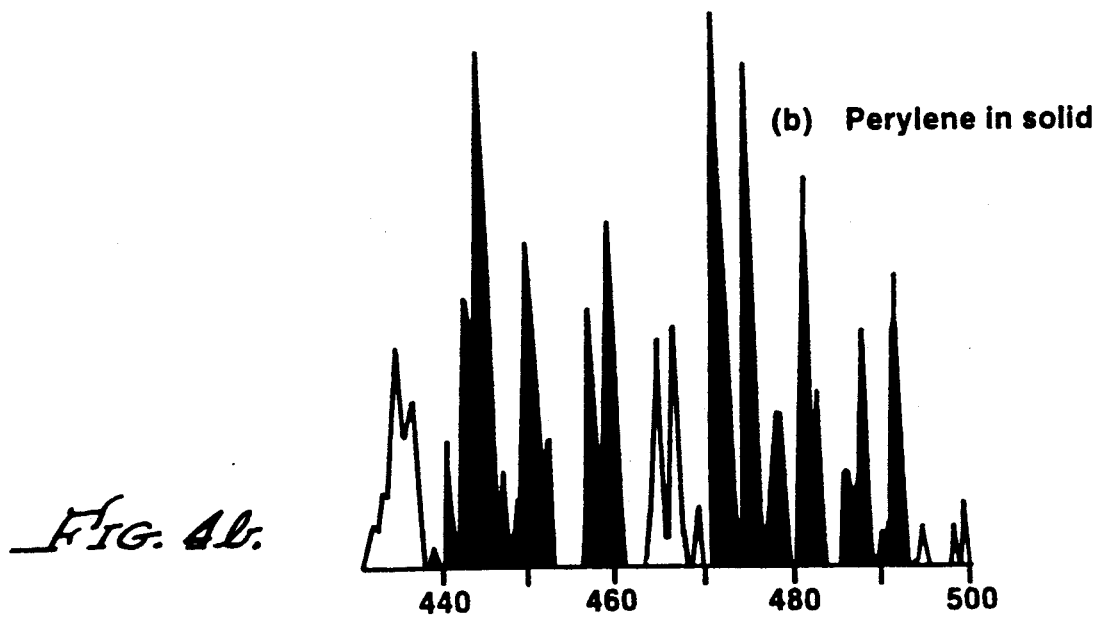

FIG. 4 shows the fluorescence spectrum of perylene sample deposited in a solvent matrix (Wehry and Mumantor, 1981) and the spectrum of a solid perylene particle sample. Spectrum (a) was excited by a dye laser at 405.9 nm and spectrum (b) at 370 nm. Precise peaks were obtained from the solvent deposited perylene as shown in the top (a) portion of FIG. 4. The broad vibronic bands have been subtracted from the spectrum shown in the lower (b) portion of FIG. 4. The baseline subtracted spectra appears to correspond roughly to published measured small peaks from perylene in a heptane matrix. The high resolution achieved provides a basis for confidence in the ability to selectively excite and detect individual compounds in multi-component samples.

Additional resolution may be obtained if the sample is also temperature controlled and cooled to cryogenic temperatures. The resolution is generally expected to improve as the temperature declines, but some shift in wavelength may be possible due to the thermal changes.

Figure 5A:
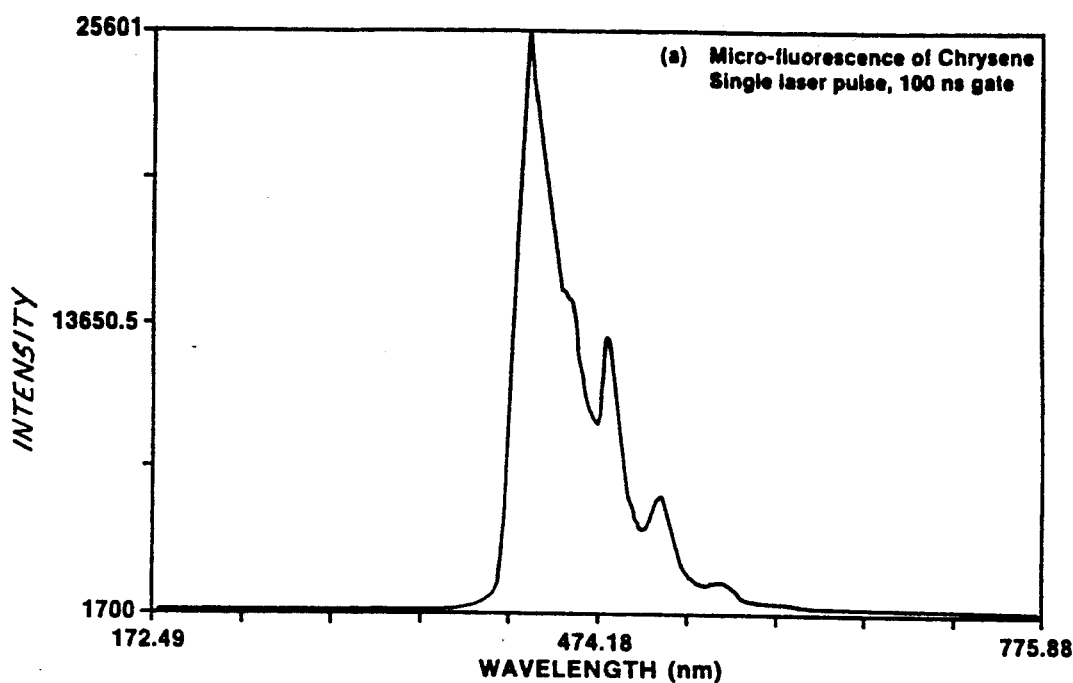
Figure 5B:
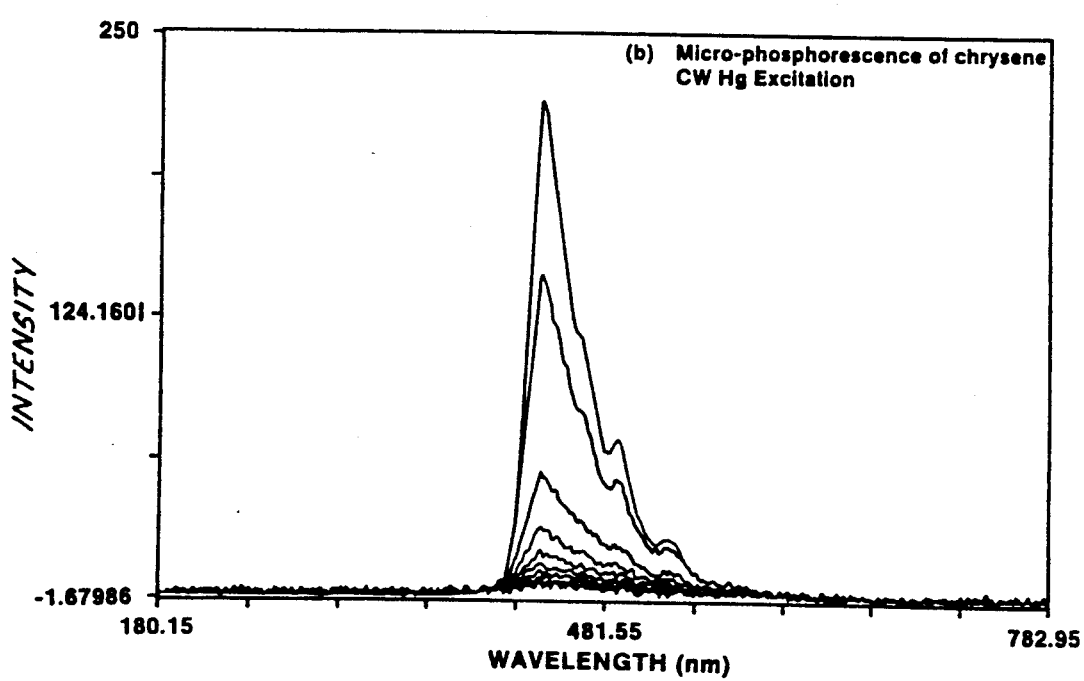

FIG. 5 shows the fluorescence and phosphorescence of solid chrysene (another PAH) measured in a polished sample pellet. The known vibronic bands are well resolved as shown in the upper (a) portion of FIG. 5. Ten gated measurements (20 ms each) were made of the phosphorescence of chrysene after continuous wave exciting by a mercury lamp ceased, as shown in the lower (b) portion of FIG. 5. The intensity of phosphorescence decreases rapidly over time, but the vibronic bands are still detectable. However, the vibronic bands do not seem to have shifts in wavelength, although the relative intensity changes over time. Although the cause of this lack of spectral shift is unknown, the gated spectral system results may again be a more accurate representation of the actual spectral structure over time.

EXAMPLE 2

Figure 6A:
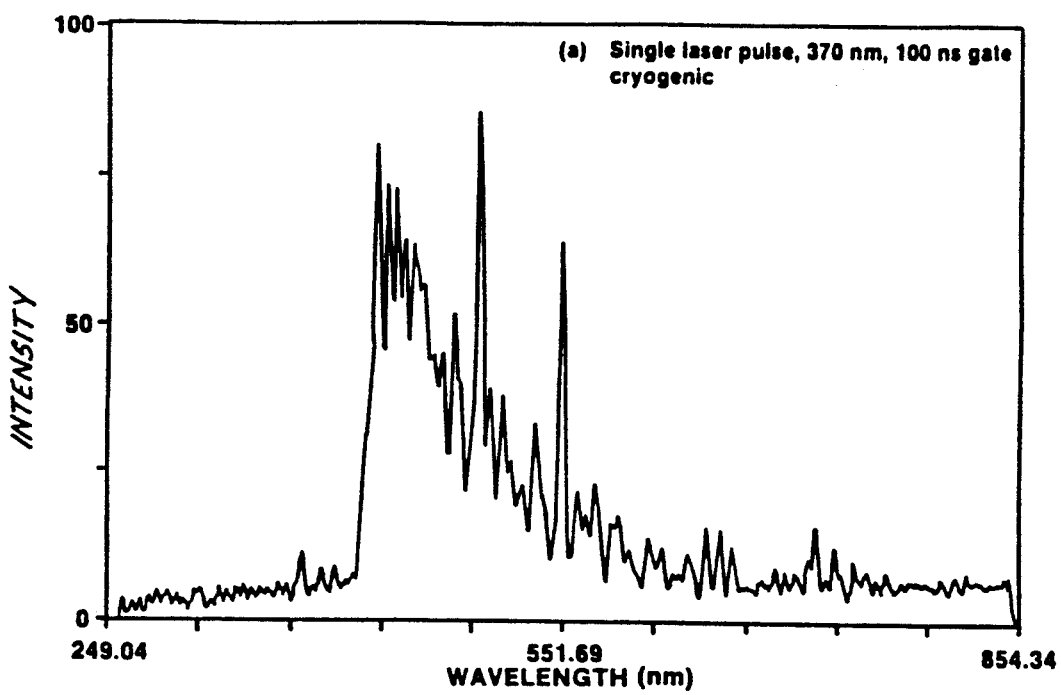
FIGS. 6a, 6b, 6c, 7a, 7b, 7c, 8a, and 8b results of using the microspectrophotometry system on kerogen particles in a geological composite sample.
Figure 6B:
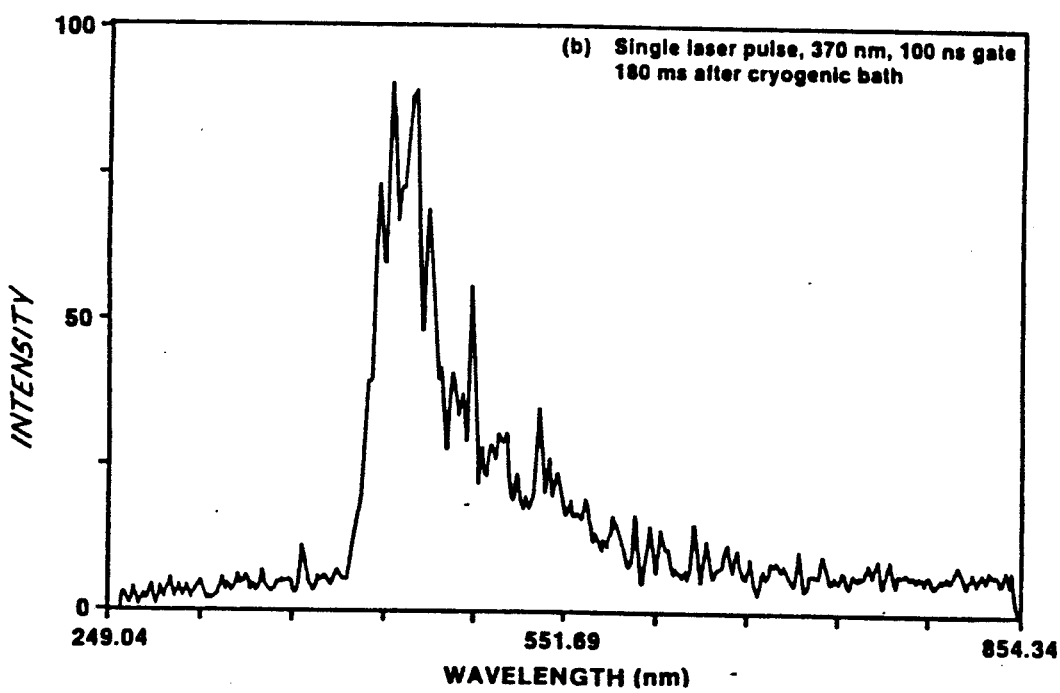
Figure 6C:
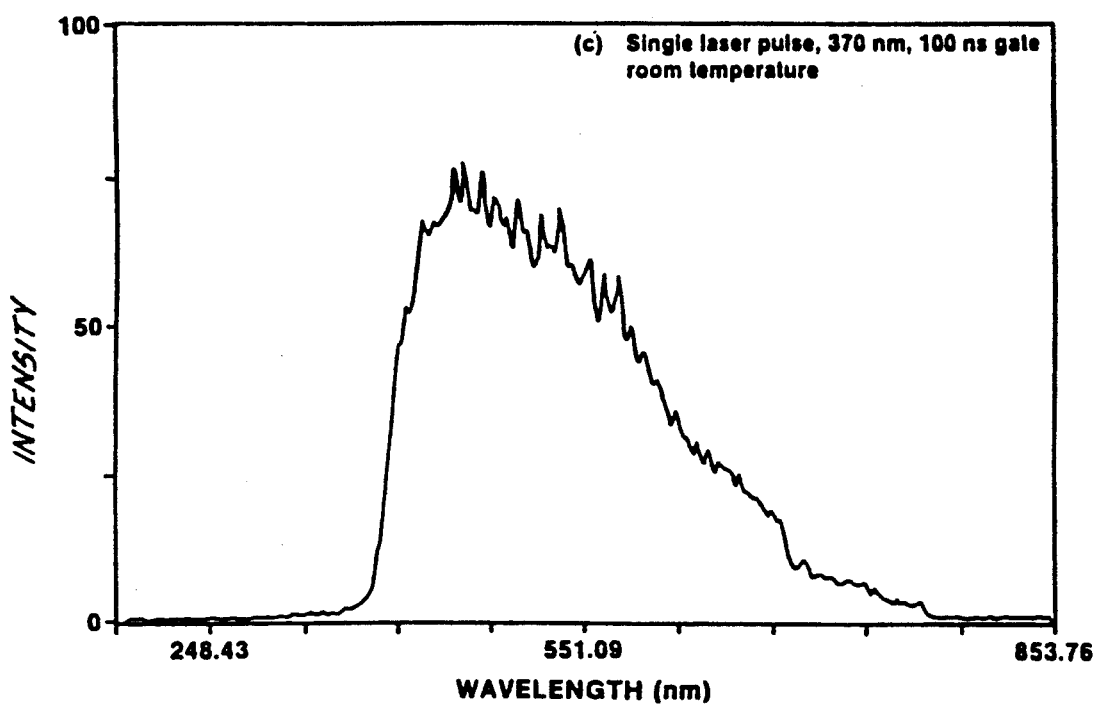
Figure 7A:
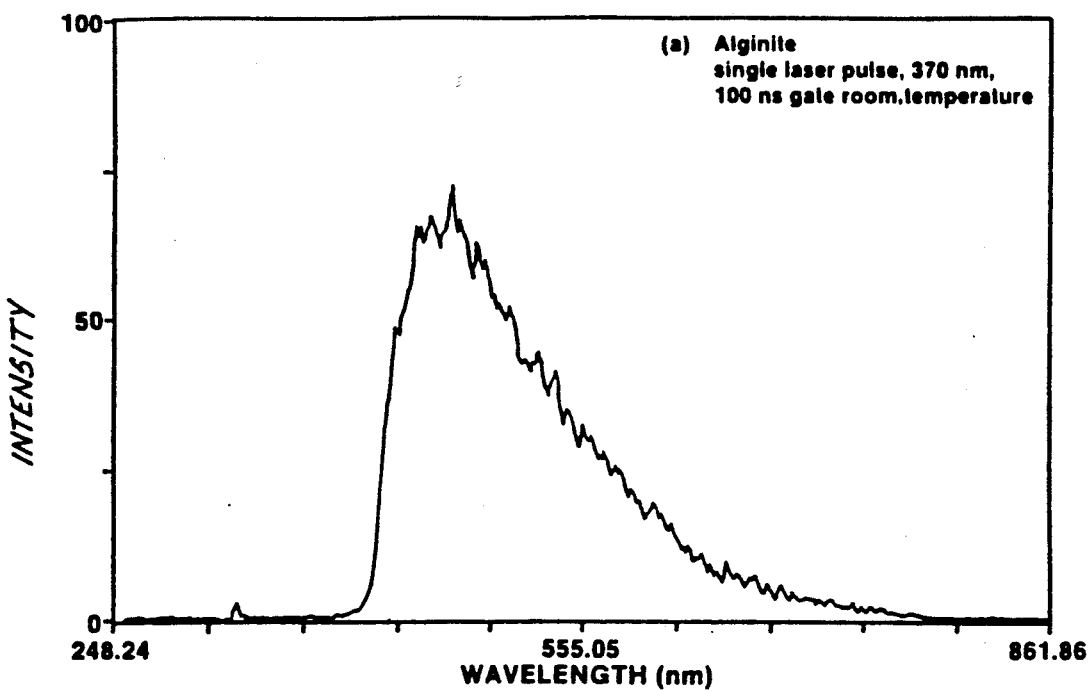
Figure 7B:
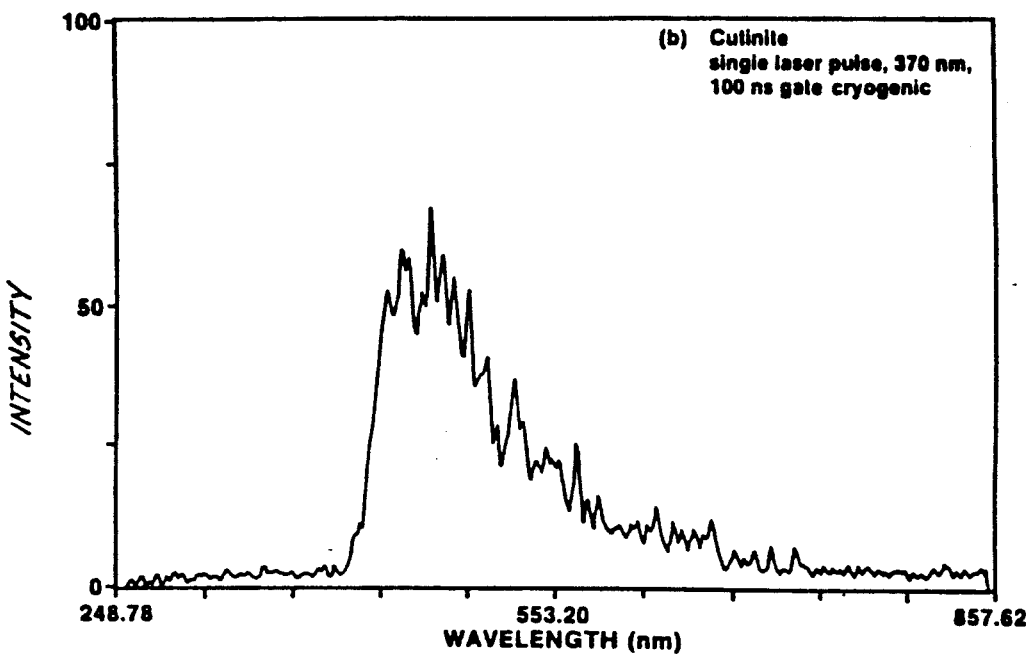
Figure 7C:
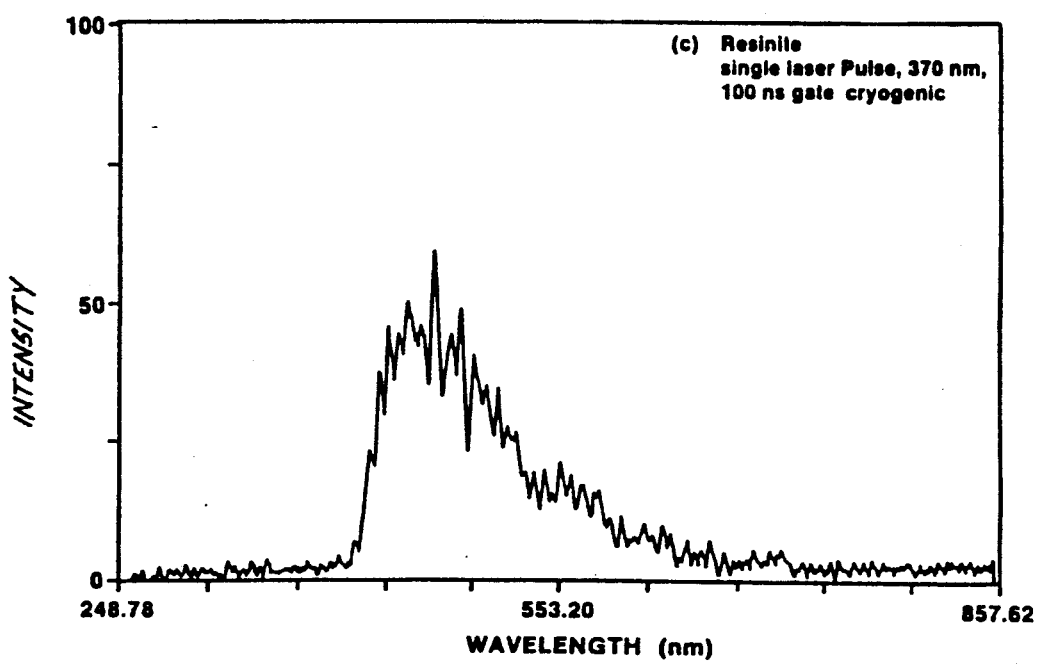
Figure 8A:
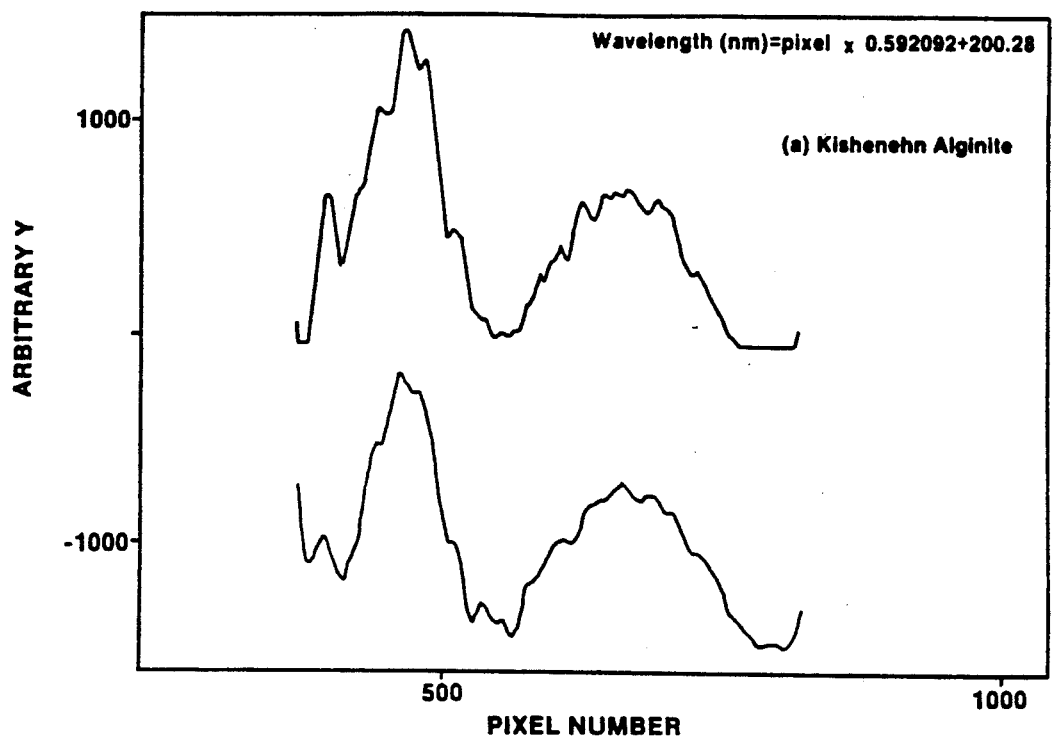
Figure 8B:
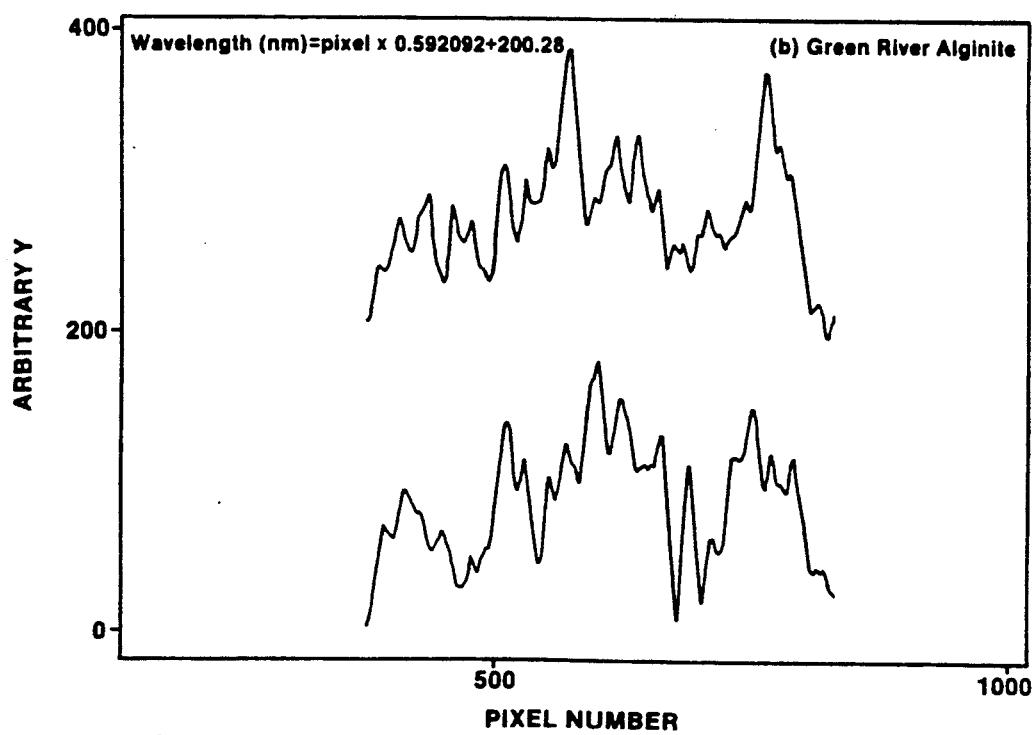

FIGS. 6-8 are the results of using the system to analyze kerogen pellet samples. The dye in the dye laser 10 was polyphenyl 1 dissolved in ethylene glycol in a concentration of 0.18 gram/liter. The repetition rate was set at 5 hertz using an exciting wavelength of 370 nanometers. Each spectrum was induced by a single laser pulse of approximately 15 nanoseconds long immediately prior to opening of the detector gate. Gate widths were 100 nanoseconds and the array detector was temperature locked at $-25°$ C.

The solid samples were composite geological samples. Particles varied between 5-10 microns in size. FIG. 6 depicts the cryogenic (a), low temperature (b) and room temperature (c) results from a filamentous alginite contained in a Green River Shale sample. FIG. 7 shows the results of different areas of interest in a Kishenehn Formation sample. FIG. 7 (a) is the graphical results from an alginite portion, FIG. 7 (b) a cutinite portion, and FIG. 7 (c) a resinite portion. FIG. 8 shows the results when broad baselines are subtracted from the acquired spectra of the aforementioned kerogen sample. The kerogen sample results show precise spectral structure and a new ability to differentiate between different samples and microscopic structures.

While the preferred embodiment of the invention has been shown and described, and some alternative embodiments also shown and/or described, changes and modifications may be made thereto without departing from the invention. Accordingly, it is intended to embrace within the invention all such changes, modifications and alternative embodiments as fall within the spirit and scope of the appended claims.

What is claimed is:

1. A method for detecting emissions from a microscopic portion of a solid sample, which method comprises:

optically viewing said microscopic portion through a microscope apparatus;

irradiating the microscopically viewed portion with an excitation pulse of radiation wherein said pulse passes through at least a portion of said microscope apparatus, said pulse essentially focused on said microscopic portion and said pulse beginning at an initial time $t_o$ and ending after a pulse width time $t_{pw}$;

detecting a radiative emission spectrum from the irradiated sample portion within a gate controlled time window, said time window beginning at a window start time $t_{ws}$ and ending after a window width time $t_{ww}$ measured from said $t_{ws}$;

wherein said $t_{ws}$ occurs after aid $t_o$; and wherein spectral changes over time may be detected.

2. A method for detecting emissions from a microscopic portion of a sample, which method comprises:

optically viewing said microscopic portion through a microscope apparatus;

irradiating the microscopically viewed portion with an excitation pulse of radiation wherein said pulse passes through at least a portion of said microscope apparatus, said pulse essentially focused on said microscopic portion and said pulse beginning at an initial time $t_o$ and ending after a pulse width time $t_{pw}$;

detecting a radiative emission spectrum from the irradiated sample portion within a gate controlled time window, said time window beginning at a window start time $t_{ws}$ and ending after a window width time $t_{ww}$ measured from said $t_{ws}$;

wherein said $t_{ws}$ occurs after said $t_o$; and wherein said pulse is within a narrow band of frequencies, said detected emission is a fluorescence spectral structure over a band of frequencies and which also comprises the step of comparing the detected fluorescence spectral structure to a reference fluorescence spectral structure.

3. The method of claim 2 wherein said pulse is a tunable output beam from a pumped dye laser and wherein said irradiating step comprises:

expanding said output beam;

collimating the expanded beam; and focusing the collimated beam onto said sample portion wherein the expanded, collimated and focused beams pass through at least a portion of said microscope.

4. The method of claim 3 wherein said sample comprises a plurality of microscopic and heterogeneous particles and said portion is substantially limited to one of said particles, and wherein said beam is directed along an axis and said focusing is capable of impinging said beam onto the surface of a particle within said sample portion, said beam impinging an area of said particle having a major dimension less than one millimeter as measured perpendicular to said axis.

5. The method of claim 4 wherein $t_{ws}$ minus to defines a window lag time $t_{wl}$ and the window times are adjustable by a detector gate controller, wherein said window width time $t_{ww}$ is adjustable from 100 nanoseconds to 10 ms, said window lag time $t_{wl}$ is adjustable from 500 nanoseconds to 3 ms.

6. The method of claim 5 wherein said pumped dye laser is pumped by a pulsed output of an excimer laser.

7. The method of claim 6 said excimer laser is a XeCl laser having a pulse width of less than about 20 nanoseconds.

8. The method of claim 7 wherein said excimer laser produces a laser beam pulse at a wavelength of less than about 400 nm having a pulse energy of at least about 200 mj.

9. The method of claim 8 wherein said excimer laser is safety interlocked with a means for access.

10. The method of claim 9 wherein said output of said pumped dye laser is tunable from 320 nm to 970 nm.

11. The method of claim 10 wherein said $t_{ws}$ occurs from 100 ns to 10 ms after said $t_o$.

12. The method of claim 11 wherein said output of said pumped dye laser is a train of laser beam pulses having a frequency of at least 1 Hz.

13. The method of claim 12 wherein said window times are synchronized by a electronic controller and said $t_{ws}$ occurs after said $t_{pw}$.

14. A microspectrophotometry apparatus for determining properties of a microscopic particle within a heterogeneous sample, said apparatus comprising:

an optical microscope for viewing said particle;

a pulsable and tunable irradiation source capable of irradiating a first portion of said particle through at least one lens of said microscope an avoiding similarly irradiating a second portion of said particle;

a radiation detector capable of detecting spectral radiative emissions from the irradiated particle through at least a portion of said microscope; and means for controlling the time said detector is capable of detecting, so as to create a time window of detecting.

15. The apparatus of claim 14 which also comprises means for optically viewing said particle and wherein said irradiation source is a beam from a pumped dye within a dye laser which can be directed to the optically viewed particle.

16. The apparatus of claim 15 which also comprises:

an exciter of said dye laser; and means for controlling temperature of said pumped dye.

17. The apparatus of claim 16 wherein said exciter is a beam from a XeCl excimer laser.

18. The apparatus of claim 17 wherein said means for controlling temperature comprises:

a source of cooling;

a conduit in thermal contact with said dye laser; and means for connecting said conduit and said source of cooling.

19. A microspectrophotometry apparatus for viewing and detecting time domain spectral emissions from a particle having a microscopic surface area when viewed, said apparatus comprising:

an optical microscope for viewing said particle;

a pulsable laser beam irradiation source capable of irradiating a first portion of an area essentially within the boundaries of said surface area through at least part of said microscope while avoiding significant irradiation of most of a second portion of said surface area; and a radiation detector capable of detecting the spectral radiative emissions from said surface area after said irradiating.

20. The apparatus of claim 19 wherein said beam irradiation source comprises:

a source of a laser beam having a representative cross-sectional area;

a laser beam expander and collimator, producing a larger cross-sectional area laser beam when said laser beam is transmitted;

an attenuator of said larger laser beam;

means for changing the direction of said larger laser beam; and means for focusing said larger laser beam onto said surface area.

21. The apparatus of claim 20 wherein said beam irradiation source also comprises:

a laser beam splitter for separating less than ten percent of the energy of said laser beam; and a laser beam energy probe and a laser beam energy meter for measuring the separated beam.

22. The apparatus of claim 21 wherein said radiation detector comprises:

a spectrograph for detecting wavelength and intensity of said emissions, said spectrograph having an entrance port;

means for collimating said emissions into an enlarged emission beam;

a barrier filter for blocking unwanted radiation wavelengths from said enlarged emission beam; and a condensing lens for focusing said enlarged emission beam to generally within said entrance port.

23. The apparatus of claim 22 wherein said radiation detector also comprises a dichroic mirror for reflecting said laser beam and transmitting said enlarged emission beam.

24. The apparatus of claim 23 which also comprises means for controlling the time said detector is capable of detecting, so as to create a time window of detecting.

* * * * *

UNITED STATES PATENT AND TRADEMARK OFFICE
CERTIFICATE OF CORRECTION

PATENT NO. : 5,252,834

DATED : Oct. 12, 1993

INVENTOR(S) : Rui Lin

It is certified that error appears in the above-identified patent and that said Letters Patent is hereby corrected as shown below:

Title page, Item [56], under References Cited, U.S. Patent Documents, add:

-- 4,616,133     10/86     Senftle     250/253 --.

Title page under Other Publications, add:

-- "Laser-Induced Fluorescence Spectrometry of Polycyclic Aromatic Hydrocarbons Isolated in Vapor-Deposited in n-Alkane Matrices," Maple, et al., American Chemical Society, Anal. Chem. 1980, Vol. 52, pp. 920-924 --.

-- "Low Temperature Fluorometric Techniques and Their Application to Analytical Chemistry in Modern Fluorescence Spectroscopy 4," by Wehry and Manatov, 1981, page 226 --.

-- "Handbook of Fluorescence Spectro of Aromatic Molecules", by Isadore B. Berlman, Academic Press, New York, 1965, pp. 258 --.

Claim 5, Column 13, line 52, delete "to" and insert therefor -- $t_o$ --.

UNITED STATES PATENT AND TRADEMARK OFFICE
CERTIFICATE OF CORRECTION

PATENT NO. : 5,252,834
DATED : Oct. 12, 1993
INVENTOR(S) : Rui Lin

It is certified that error appears in the above-indentified patent and that said Letters Patent is hereby corrected as shown below:

Claim 14, Column 14, line 17, delete "an" and insert therefor --and --.

Signed and Sealed this

Twenty-fourth Day of January, 1995

Attest:

BRUCE LEHMAN

*Attesting Officer*  *Commissioner of Patents and Trademarks*